United States Patent [19]

Picklesimer

[11] 4,226,800

[45] Oct. 7, 1980

[54] SYNTHESIS OF ACETYLENE-TERMINATED COMPOUNDS

[75] Inventor: Lewellyn G. Picklesimer, Dayton, Ohio

[73] Assignee: The United States of America as represented by the Secretary of the Air Force, Washington, D.C.

[21] Appl. No.: 48,322

[22] Filed: Jun. 14, 1979

[51] Int. Cl.$^2$ .................. C07C 43/20; C07C 121/75; C07C 147/06; C08F 138/00
[52] U.S. Cl. ................................ 260/465 F; 525/502; 528/86; 528/171; 528/210; 528/219; 568/636; 568/638; 568/641; 568/651; 568/654; 568/720; 568/723; 568/766; 568/33; 568/48
[58] Field of Search ........ 260/465 F, 607 AR, 609 F; 568/636, 641, 654; 525/502

[56] References Cited

U.S. PATENT DOCUMENTS 4,141,921  2/1979  Karrer ................................ 568/636

OTHER PUBLICATIONS

Fletcher et al., J. Amer. Chem. Soc., vol. 65, pp. 1431–1432 (1943).
Hay et al., Polymer Letters, 8, pp. 97–99 (1970).

*Primary Examiner*—Dolph H. Torrence
*Attorney, Agent, or Firm*—Joseph E. Rusz; Cedric H. Kuhn

[57] ABSTRACT

Phenolic materials containing propargyl groups are prepared by reacting a polyhydric, phenolic material with propargyl bromide, the reaction being conducted in an aqueous sodium hydroxide solution. The products can be thermally polymerized to polymers which are useful as adhesives and as matrix resins in the fabrication of composites.

13 Claims, No Drawings

SYNTHESIS OF ACETYLENE-TERMINATED COMPOUNDS

RIGHTS OF THE GOVERNMENT

The invention described herein may be manufactured and used by or for the Government of the United States for all governmental purposes without the payment of any royalty.

FIELD OF THE INVENTION

This invention relates to the preparation of aromatic materials containing propargyl groups. In one aspect, it relates to polymers prepared from the aromatic materials.

BACKGROUND OF THE INVENTION

Acetylene-terminated compounds show promise for use in the preparation of matrix resins and adhesives for advanced aircraft and aerospace systems. The compounds can be polymerized thermally without the evolution of volatile by-products, thereby obviating the problem of void formation in composite structures and molded articles.

In Polymer Letters, 8, 97–99 (1970), A. S. Hay et al. describe the preparation of bispropargyl ethers of bisphenols by reacting a bisphenol with propargyl bromide in acetone in the presence of potassium carbonate. The reactions are characterized by long reaction times. For example, when using 4,4'-isopropylidenedi-phenol (bisphenol A) as the bisphenol, the time of reaction at reflux temperature was 72 hours. It would be desirable to have a process for preparing bispropargyl ethers of bisphenols that could be carried out in short reaction periods in a non-polluting reaction medium.

It is a principal object of this invention, therefore, to provide an improved process for preparing bispropargyl ethers of phenolic materials.

Another object of the invention is to provide aromatic compounds containing propargyl and hydroxy groups.

A further object of the invention is to provide polymers prepared from aromatic compounds containing propargyl groups.

Other objects and advantages of the invention will be apparent to those skilled in the art upon consideration of the accompanying disclosure.

SUMMARY OF THE INVENTION

The present invention resides in a process for preparing phenolic materials containing propargyl groups. In accordance with the process, a polyhydric, phenolic material is reacted with propargyl bromide in an aqueous sodium hydroxide solution. The reaction occurs at the interface between the aqueous basic solution of the phenolic material and the propargyl bromide which is insoluble in water. The reaction that occurs is illustrated by the following equation:

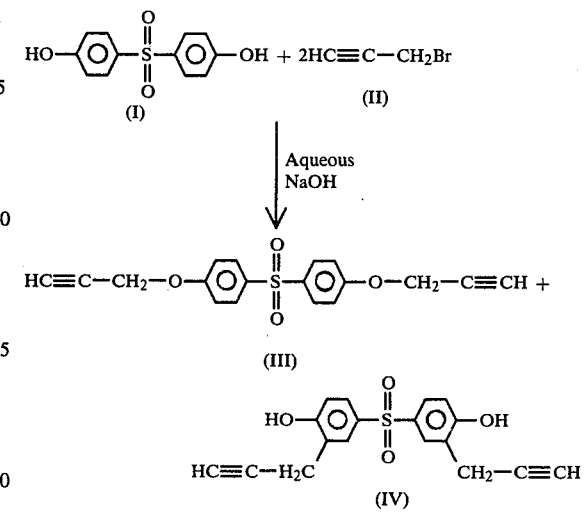

As shown by the foregoing equation, an exemplary phenolic material, namely, 4,4'-dihydroxydiphenyl sulfone (I), is reacted with propargyl bromide (II) in an aqueous sodium hydroxide medium. As a result of the reaction, two products are formed, i.e., the dipropargyloxy ether of sulfonyldiphenol (III) and dipropargyl-sulfonyldiphenol (IV). Compound (III) is insoluble in the aqueous medium whereas compound (IV) is soluble therein. In general, compound (III) is obtained in a major amount that can be separated from the reaction mixture by any suitable means, e.g., by filtration or decantation. The soluble compound (IV) can be recovered by acidifying the basic aqueous solution, which remains after separation of the solid product, with concentrated hydrochloric acid. As a result of this treatment, there is obtained a solid compound (IV) which can be purified by crystallization. In this procedure, the compound is dissolved in an alcohol, such as methanol, after which the solution is poured into water, thereby causing the compound to crystallize.

Various polyhydric, phenolic materials can be utilized in conducting the process of this invention. Examples of such materials include mononuclear, polyhydric phenols, such as resorcinol, hydroquinol, 2,3-dicyanohydroquinone, and the like, as well as polyhydric, polynuclear phenols having the formula:

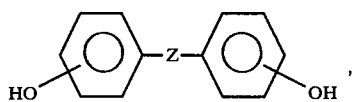

wherein Z is a divalent radical, such as —O—, —S—,

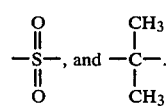

It is often preferred to use 4,4'-dihydroxydiphenyl-sulfone and 4,4'-isopropylidenediphenol (bisphenol A).

It is also within the scope of the invention to utilize phenolic resins, such as phenol novolac and resorcinol novolac resins having, respectively, the following formulas:

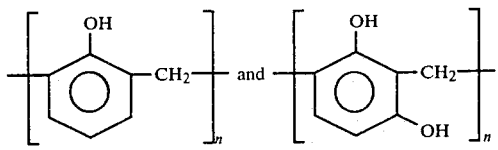

In the foregoing formulas, n is an integer ranging from about 2 to 100. It is generally preferred to use a resin in which n ranges from 5 to 10.

The amount of propargyl bromide used is about equivalent to the hydroxyl content of the polyhydric phenol. Thus, the mole ratio of propargyl bromide to polyhydric phenol is about 2:1. However, it is within the scope of the invention to use an excess of the propargyl bromide so that the mole ratio of propargyl bromide to polyhydric phenol ranges from 2:1 to 2.5:1.

When a novolac resin is used, the amount of propargyl bromide used depends upon the number of hydroxyls available for etherification and the degree of etherification desired. Thus, the amount of propargyl bromide can vary within rather broad limits up to a maximum amount which is the equivalent or slightly in excess, e.g., 5 to 10 percent, of the equivalent to the hydroxyl content of the novolac resin. In general, the higher the degree of etherification the higher is the crosslink density of the cured resin.

The amount of sodium hydroxide used is equivalent to the total number of hydroxyls that it is desired to etherify. Thus, equimolar amounts of sodium hydroxide and propargyl bromide can be advantageously employed in the present process. When using equimolar amounts, a maximum amount of the product containing propargyl ether groups is obtained. A larger amount of the product containing hydroxyl and propargyl groups is produced if an excess of sodium hydroxide is utilized.

As indicated above, the reaction of the phenolic material and propargyl bromide is conducted in an aqueous sodium hydroxide solution. The reaction temperature ranges from about 70° C. to the reflux temperature of the base solution, i.e., about 100° C. The reaction is complete when the aqueous solution is neutral. Under reflux condition a reaction period of about 1 hour is sufficient while at lower temperatures a reaction period up to about 3 hours is required.

In a preferred procedure for carrying out the process, the propargyl bromide is added to the phenolic material dissolved in the basic solution. The propargyl bromide can be added directly by itself or in solution in a suitable solvent. Since the propargyl bromide is often supplied in solution in toluene, it is usually preferred to add it as received from the supplier. However, other solvents can be used so long as they are immiscible with water and have a boiling point of at least 80° C. The product containing propargyl ether groups is insoluble in the reaction medium whereas the product containing hydroxyls is soluble in the medium. The products can be readily recovered in the manner described above.

The products prepared by the process of this invention can be converted to polymers by thermal polymerization of the acetylene groups. A temperature of at least 200° C. is usually required for the polymerization. The polymers obtained are useful as adhesives and as matrix resins in the fabrication of composites. Since volatile by-products are not evolved during the polymerization, the composites are free of undesirable voids.

A more complete understanding of the invention can be obtained by referring to the following illustrative examples which are not intended, however, to be unduly limitative of the invention.

EXAMPLE I

A run was carried out in which the dipropargyloxy ether of sulfonyldiphenol was prepared in accordance with the present process. The following ingredients in the amounts indicated were utilized:

| 4,4'-Dihydroxydiphenyl sulfone | 25.0 g | 0.1 mole |
|---|---|---|
| Propargyl bromide | 26.18 g. | 0.2 mole plus 10% excess |
| Sodium hydroxide | 8.0 g | 0.2 mole |

The 4,4'-dihydroxydiphenyl sulfone and sodium hydroxide were dissolved in 200 ml of water in a reaction flask fitted with a stirrer, dropping funnel and reflux condenser. The solution was heated to reflux and the propargyl bromide was added slowly. A vigorous reaction occurred when the propargyl bromide was added, and a white product started to separate. After addition of the propargyl bromide, refluxing was continued for one hour. The product was separated by filtration and then dissolved in hot acetone. Upon cooling the product crystallized, yielding 16.1 g (49.4% yield).

Analysis calc'd for $C_{18}SO_4H_{14}$: C,66.26; S,9.82; H,4.29. Found: C,65.79; S,10.10; H,4.15.

Melting point: 185°–186° C.

The product was thermally polymerized by heating at 210° C. for a period of 12 hours. A hard, black polymer was obtained. During the polymerization there was no evolution of volatile by-products.

EXAMPLE II

A run was conducted in which the dipropargyloxy ether of sulfonyldiphenol was prepared by utilizing the following ingredients in the amounts indicated:

| 4,4'-Dihydroxydiphenyl sulfone | 25.0 g | 0.1 mole |
|---|---|---|
| Propargyl bromide | 26.18g | 0.2 mole plus 10% excess |
| Sodium hydroxide | 8.0 g | 0.2 mole |

The procedure of Example I was followed except that the propargyl bromide was added dropwise at room temperature over a period of 30 minutes. The mixture was stirred at room temperature for 2 hours and very little, if any, reaction occurred as indicated by the absence of product and the basic pH of the aqueous phase. The mixture was heated rapidly to 90° C. and at about 70° C. product began to separate. After 30 minutes at 90° C., the aqueous phase was neutral, indicating completion of the reaction. The product was isolated by filtration. The weight of the dried product was 30.8 g (99.4% yield). The melting point of crystallized product was 185°–186° C.

EXAMPLE III

A run was carried out in which the dipropargyloxy ether of sulfonyldiphenol was prepared with the following ingredients in the amounts indicated:

| 4,4'-Dihydroxydiphenyl sulfone | 73.0 g | 0.3 mole |
|---|---|---|
| Propargyl bromide | 71.4 g | 0.6 mole |

-continued

| | | |
|---|---|---|
| Sodium hydroxide | 24.0 g | 0.6 mole |

The 4,4'-dihydroxydiphenyl sulfone and the sodium hydroxide were dissolved in 600 ml of water in a reaction flask fitted with a stirrer and condenser. The propargyl bromide was added in one addition as an 80 percent solution in toluene. The mixture was heated rapidly with stirring to 82° C. and maintained at that temperature for one hour at which time the reaction was complete as indicated by the neutral pH of the aqueous phase. The product was separated by filtration and washed twice with methanol. The amount of the solid phase was 67 g for a yield of 68 percent.

The methanol wash was added to water, thereby causing the precipitation of a gummy solid. After separation, the dried product weighed 13.0 g for a yield of 13.3 percent. The infrared spectra of the product confirmed the dipropargyl compound of 4,4'-dihydroxydiphenyl sulfone, and also gave absorption bands confirming the presence of hydroxyl groups.

EXAMPLE IV

A run was conducted in which the dipropargyloxy ether of sulfonyldiphenol was prepared with the ingredients listed below. In this run a large excess of sodium hydroxide was used.

| | | |
|---|---|---|
| 4,4'-Dihydroxydiphenyl sulfone | 25.0 g | 0.1 mole |
| Propargyl bromide | 23.8 g | 0.2 mole |
| Sodium hydroxide | 16.0 g | 0.4 mole |

The 4.4'-dihydroxydiphenyl sulfone and sodium hydroxide were dissolved in 600 ml of water. The propargyl bromide as an 80 percent solution in toluene was added in one addition to the reaction flask. The mixture was brought rapidly to reflux with stirring and maintained at reflux for 2 hours. The mixture was filtered and 4.2 g (13% yield) of the bispropargyl ether was obtained.

The aqueous filtrate was made acid with hydrochloric acid, and a brown resin was obtained. The dried weight of the resin was 19.5 g for a yield of 60 percent. The resin was dissolved in methanol and then crystallized by pouring the solution into water. The light brown crystalline product obtained had a melting point of 154°–158° C. The infrared spectra of this compound confirmed that it was the dipropargyl compound of the diphenyl sulfone, and showed a strong absorption band for the hydroxyl group.

The compound described in the preceding paragraph was thermally polymerized to a hard polymer by heating at 210° C. During the polymerization there was no evolution of volatile by-products.

EXAMPLE V

A run was conducted in which the bispropargyl ether of 2,3-dicyanohydroquinone was prepared, utilizing the following ingredients in the indicated amounts:

| | | |
|---|---|---|
| 2,3-Dicyanohydroquinone | 32.0 g | 0.2 mole |
| Propargyl bromide | 47.6 g | 0.4 mole |
| Sodium hydroxide | 16.0 g | 0.4 mole |

The 2,3-dicyanohydroquinone and sodium hydroxide were dissolved in 50 ml of water in a flask fitted with a stirrer and reflux condenser. The propargyl bromide was added to the reaction flask in one addition as an 80 percent solution in toluene. The temperature was raised rapidly to 80° C. with stirring. The product began to separate almost immediately. Heating and stirring was continued for one hour. At this time the aqueous phase was neutral, indicating completion of the reaction. The product was separated by filtration and washed several times with water. The product was a brown powder and after drying weighed 34.7 g (73.5% yield).

Infrared spectra showed absorption bands at 2230 cm$^{-1}$ for nitrile and at 3300 and 2130 cm$^{-1}$ for acetylene.

EXAMPLE VI

A run was carried out in which a resorcinol novolac was used as the phenolic material in the process of this invention. The following materials were used in the run:

Resorcinol novolac: 24.4 g
Propargyl bromide: 23.8 g
Sodium hydroxide: 8.0 g

The novolac resin and sodium hydroxide were dissolved in 200 ml of water in a reaction flask and heated to reflux. The propargyl bromide was added dropwise with stirring over a 30 minute period. The aqueous phase was neutral almost immediately, indicating completion of the reaction. Refluxing was continued for 1.25 hours after addition of the propargyl bromide. A dark red product was separated by decantation of the aqueous phase. The product was dissolved in a solution of 300 ml of water containing 8 g of sodium hydroxide and filtered. The filtrate was neutralized with concentrated hydrochloric acid, and the precipitate that formed was separated by filtration. After drying overnight in vacuo at 65° C., the product weighed 21.1 g (66% yield). Infrared spectra confirmed the presence of propargyl ether groups.

The product was thermally polymerized at 200° C. to a hard resin. During the polymerization there was no evolution of volatiles.

EXAMPLE VII

A run was conducted in which bisphenol A was employed as the phenolic material in the present process. The amounts of the materials used were as follows:

| | | |
|---|---|---|
| Bisphenol A | 228 g | 1.0 mole |
| Propargyl bromide | 238 g | 2.0 moles |
| Sodium hydroxide | 80 g | 2.0 moles |

The bisphenol A and sodium hydroxide were dissolved in 1 liter of water in a reaction flask. The propargyl bromide was added in one addition as an 80 percent solution in toluene. The mixture was heated rapidly to reflux and refluxed for 2.5 hours. The aqueous phase was neutral at this point, indicating completion of the reaction. The product was separated as a dark resinous liquid by means of a separatory funnel. The toluene was allowed to evaporate and the product was extracted with 500 ml of 2-propanol. The 2-propanol insoluble material was dried and weighed 138.0 g (45.4% yield). The product was the bispropargyl ether of bisphenol A as indicated by a melting point of 84°–85° C. and infrared spectra.

The 2-propanol extract was mixed with water, thereby causing a resinous material to precipitate. After separation and drying, the material weighed 132.5 g (43.6% yield). This product was soluble in hot aqueous sodium hydroxide, indicating the presence of hydroxyl groups. The basic solution was cooled and the solid product filtered and neutralized with concentrated hydrochloric acid. The product upon drying was a very viscous semisolid. The infrared spectra confirmed the presence of propargyl groups as well as hydroxyl groups.

The product described in the preceding paragraph was thermally polymerized at about 200° C. to a hard solid. During the polymerization there was no evolution of volatiles.

As seen from the foregoing, the present invention provides an improved process for preparing phenolic materials containing reactive propargyl groups. The process is characterized by short reaction times and the utilization of an aqueous reaction medium. Since the propargyl groups contain acetylene linkages, the products can be polymerized without the evolution of undesirable, void-forming by-products. The products are as a result eminently suitable for use in forming matrices for fiber-reinforced composites.

As will be evident to those skilled in the art modifications of the present invention can be made in view of the foregoing disclosure without departing from the spirit and scope of the invention.

I claim:

1. A process for preparing a phenolic material containing propargyl groups which comprises reacting a polyhydric, phenolic material with propargyl bromide, the reaction being carried out in an aqueous sodium hydroxide solution.

2. The process according to claim 1 in which the reaction is conducted at a temperature ranging from about 70° C. to reflux temperature of the aqueous solution for a period of about 1 to 3 hours.

3. The process according to claim 2 in which the polyhydric, phenolic material is selected from the group consisting of a polyhydric, mononuclear phenol; a polyhydric, polynuclear phenol; and a phenolic resin.

4. The process according to claim 3 in which the polyhydric, mononuclear phenol is resorcinol, hydroquinol or 2,3-dicyanohydroquinone.

5. The process according to claim 3 in which the polynuclear, polyhydric phenol has the following formula:

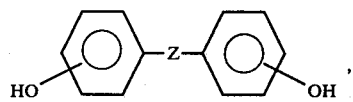

wherein Z is —O—, —S—,

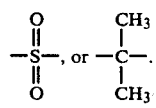

6. The process according to claim 3 in which the phenolic resin is a phenol novolac resin or a resorcinol novolac resin.

7. The process according to claim 3 in which the amount of propargyl bromide is about equivalent to the hydroxyl content of the phenolic material and the mole ratio of sodium hydroxide to propargyl bromide is about 1:1.

8. A process for preparing a phenolic compound containing propargyl ether groups which comprises reacting propargyl bromide with a polyhydric phenol selected from the group consisting of 4,4'-dihydroxydiphenyl sulfone and 4,4'-isopropylidenediphenol, the reaction being conducted in an aqueous sodium hydroxide solution at a temperature ranging from about 70° C. to reflux temperature of the sodium hydroxide solution for a period of about 1 to 3 hours.

9. The process according to claim 8 in which the mole ratio of propargyl bromide to polyhydric phenol ranges from 2:1 to 2.5:1 and the mole ratio of sodium hydroxide to propargyl bromide is 1:1.

10. A process for preparing a phenolic material containing propargyl groups which comprises reacting propargyl bromide with a polynuclear, polyhydric phenol having the following formula:

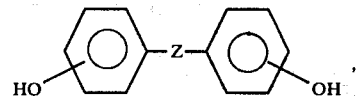

wherein Z is —O—, —S—,

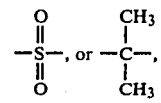

the reaction being conducted in an aqueous sodium hydroxide solution at a temperature ranging from about 70° C. to reflux temperature of the sodium hydroxide solution for a period of about 1 to 3 hours, the mole ratio of propargyl bromide to polyhydric phenol ranging from 2:1 to 2.5:1, and the mole ratio of sodium hydroxide to propargyl bromide being about 1:1.

11. The process according to claim 10 in which the polynuclear, polyhydric phenol is 4,4'-dihydroxydiphenyl sulfone.

12. The process according to claim 10 in which the polynuclear, polyhydric phenol is 4,4'-isopropylidenediphenol.

13. A process for preparing a phenolic material containing propargyl groups which comprises reacting propargyl bromide with a phenolic material selected from the group consisting of resorcinol, hydroquinol, 2,3-dicyanohydroquinone, 4,4'-dihydroxydiphenylsulfone, 4,4'-isopropylidenediphenol, a phenol novolac resin having the following formula:

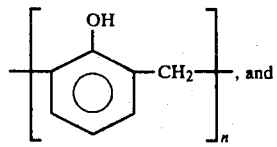

a resorcinol novolac resin having the following formula:

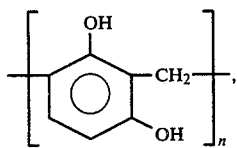

wherein n in each formula is an integer ranging from about 2 to 100, the reaction being conducted in an aqueous sodium hydroxide solution at a temperature ranging from about 70° C. to reflux temperature of the sodium hydroxide solution for a period of about 1 to 3 hours, the amount of propargyl bromide being about equivalent to the hydroxyl content of the phenolic material, and the mole ratio of sodium hydroxide to propargyl bromide being about 1:1.

* * * * *